United States Patent [19]
Yang et al.

[11] Patent Number: 5,928,664
[45] Date of Patent: Jul. 27, 1999

[54] CONSUMABLE GUMMY DELIVERY SYSTEM

[75] Inventors: Robert K. Yang, Flushing, N.Y.; T. Victor Oh, Annandale, Va.

[73] Assignee: Fuisz Technologies Ltd., Chantilly, Va.

[21] Appl. No.: 09/022,244

[22] Filed: Feb. 11, 1998

[51] Int. Cl.⁶ ..................................................... A61K 9/68
[52] U.S. Cl. .......................... 424/440; 424/441; 424/465; 424/484; 514/948
[58] Field of Search ..................................... 424/441, 404, 424/440, 465; 514/948

[56] References Cited

U.S. PATENT DOCUMENTS

| | | | |
|---|---|---|---|
| 4,879,108 | 11/1989 | Yang et al. | 424/440 |
| 4,882,159 | 11/1989 | Yang et al. | 424/440 |
| 4,882,160 | 11/1989 | Yang et al. | 424/440 |

*Primary Examiner*—Thurman K. Page
*Assistant Examiner*—D. Faulkner
*Attorney, Agent, or Firm*—John F. Levis

[57] ABSTRACT

The present invention provides consumable, gummy delivery systems and methods of making the same. The gummy delivery systems include an active ingredient admixed with a glycerylated gelatin matrix prepared by heating an aqueous solution of gelatin and glycerin to a temperature and for a time sufficient to remove some of the moisture content of the initial aqueous solution. The active ingredient can be delivered from a shearform matrix carrier.

35 Claims, No Drawings

CONSUMABLE GUMMY DELIVERY SYSTEM

BACKGROUND OF THE INVENTION

The present invention relates to novel delivery systems for actives and methods of preparation. More particularly, this invention relates to a consumable gummy delivery system for active ingredients such as medicaments, flavors, sweeteners and flavors.

Numerous delivery systems are available in the market for delivery of active ingredients. Administering actives from a chewable delivery system is a highly desirable way of delivering readily soluble actives directly from the oral cavity into the stomach. For example, chewing gum compositions generally include a water insoluble chewable gum base, such as chicle or a substitute therefor, and natural or synthetic elastomeric resins. One deficiency of using a conventional chewing gum as a delivery system for actives stems is that the gum base itself is not water soluble and always remains in the mouth as a bolus or wad, which must be disposed of. In addition, many actives may have affinity with the gum base; therefore, accurately measuring the active dosage by the base becomes difficult, if not impossible.

Other chewable delivery systems are disclosed in U.S. Pat. Nos. 4,879,108 and 4,882,159 to 4,882,160. These references disclose chewable, semi-solid delivery systems for actives which, upon losing water, become brittle and crumble. The delivery systems disclosed in these references are obtained by admixing precoated actives with a confectionery material prepared by forming a solution of gelatin, glycerin, sweeteners and about 1% to about 30% by weight water. The confectionery material functions to provide moisture to the remaining components of the delivery system. Removing water from the material will cause it to loose its chewing character and become brittle and crumbly. The delivery systems are prepared without excessive heat and when used, heat binds the moisture to the active ingredient.

Another drawback of chewable delivery systems is the tendency of losing their bulk quickly, as well as their springiness and ability to bounce back upon prolonged mastication. Thus, these systems provide virtually no capability of prolonged release of the active. Moreover, certain organoleptic appeal is lost.

It is therefore, an object of the present invention to provide new delivery systems for actives which are gummy and which overcome of the drawbacks of delivery systems currently available.

SUMMARY OF THE INVENTION

The present invention is a new consumable, gummy delivery system which includes an elastic, continuous glycerylated gelatin matrix admixed with an active ingredient. The resulting delivery system is readily soluble in aqueous media.

The elastic continuous glycerylated gelatin matrix of the present invention is prepared by dissolving a precalculated amount of an aqueous solution of gelatin, and then glycerine is added and heated to a temperature and for a time sufficient to remove from about 10% to about 100% of initial moisture content. Unless otherwise stated, all percentages herein are based on weight. In the delivery system of the present invention, the glycerylated gelatin matrix is present in an amount from about 2% to about 70% and preferably from about 10% by weight to about 35% by weight of the gummy delivery system. The gelatin is present in the an amount from about 2% to about 50% by weight, preferably from about 5% by weight to about 30% by weight of the gummy delivery system. Glycerine is present in an amount from about 4% by weight to about 60% by weight and preferably from about 10% by weight to about 50% by weight of the gummy delivery system.

Many active ingredients can be admixed with the glycerylated gelatin matrix in order to form a consumable, gummy delivery system which is readily soluble in aqueous media. Active ingredients include medicaments, flavors, sweeteners and mixtures thereof. These actives will comprise the remainder of the gummy delivery system.

The glycerylated gelatin matrix of the present invention can be further admixed with other food grade additives such as fats, medium chain triglycerides, sweeteners, flavors, colorings, humectants, fillers, emulsifiers, thickeners, and mixtures thereof.

In a preferred embodiment, the active ingredient which is admixed with the glycerylated gelatin matrix of the present invention, is provided as a component of a shearform matrix carrier prepared by flashflow processing of a feedstock comprising an active ingredient and a carrier material.

A primary component of the shearform matrix carrier can be a saccharide-material such as sucrose, corn syrup solids, water soluble cellulosics and mixtures thereof.

In another preferred embodiment, the glycerylated gelatin matrix can be provided as a component of a shearform matrix, wherein the shearform matrix includes carrier material such as saccharides, water soluble cellulosics and mixtures thereof.

The present invention also provides methods of preparing consumable, gummy delivery systems. Such methods include admixing the elastic, continuous glycerylated gelatin matrix with an active ingredient to form a homogenous mixture which is elastic, continuous and readily soluble in aqueous media. The glycerylated gelatin matrix of the present invention is prepared by heating an aqueous solution of gelatin and glycerine to a temperature and for a time sufficient to remove from about 10% to about 80% of the initial moisture content of the aqueous solution. In a preferred embodiment, it is possible to remove about 50% to about 80% of this initial moisture content. In an especially preferred embodiment the moisture content of the glycerylated gelatin matrix can be reduced completely to about 0% of the initial moisture content of the aqueous solution of gelatin and glycerin.

As a result of the present invention, delivery systems for actives are provided which have the ability of retaining moisture and, at the same time, of retaining resiliency or elasticity by bouncing back upon prolonged mastication. Moreover, the delivery systems of the present invention are entirely consumable such that no residue is left in the mouth upon use.

Other improvements which the present invention provides over the prior art will be identified as a result of the following description which sets forth the preferred embodiments of the present invention. The description is not in any way intended to limit the scope of the present invention, but rather only to provide working examples of the present preferred embodiments. The scope of the present invention will be pointed out in the appended claims.

DETAILED DESCRIPTION OF THE INVENTION

The present invention is a consumable, delivery system for actives characterized by a gummy organoleptic presentation. The gummy presentation can be described as a continuous mass having a "lay flat" quality against the teeth and a degree of elasticity sufficient to reconstitute the mass after each chew. The "gummy" perception referred to herein includes a "long texture" which means the material does not readily separate to form shortened masses during chewing. Of course when the material is degraded after continuous chewing, the mass will break down and separate into reduced-size masses. A "long-texture" mass can also be described by comparison to a short textured material which can be perceived as, among other characteristics, crumbly. "Lay flat quality" is a characteristic of a material to readily deform under the force of chewing to assume the surface contour of the teeth. Some consumers may associate the quality with softness. In any event, this quality is pleasing to most consumers. "Gummy" as used herein also means the material has a certain degree of "memory" or elasticity. Once the material is chewed and thereby pressed against the surface of a tooth (or teeth), continued chewing would quickly erode and separate the mass of material between the teeth. When the material is elastic, however, it reforms to reconstitute as a mass between the teeth. This provides a "new" mass, as it were, for subsequent chewing. Thus, "gummy" as defined herein means a longer texture, somewhat elastic material having a lay flat quality which in combination enables and entices the consumer to continue chewing and, thereby deliver the active.

The gummy material of the present invention is a glycerylated gelatin matrix provided by first adding an aqueous gelatin solution to glycerin. The resulting mixture is then heated from about 85° C. to just below 100° C. to remove at least from about 10% to about 80% by weight of the initial moisture content. In a preferred embodiment, it is contemplated to remove in excess of about 50% to about 80% of the initial moisture content. In an especially preferred embodiment the entire initial moisture content of the aqueous gelatin solution is eliminated such that the moisture content of the glycerylated gelatin matrix is about 0%. The resulting product is the glycerylated gelatin matrix of the present invention. Although there are no conventional gels, such as pectin or the like, present in the glycerylated gelatin matrix of the present invention, because of its gummy consistency, the glycerylated gelatin matrix can release an active uniformly over a long period of time. The glycerylated gelatin of the present invention can be shaped into suitable shapes. Readily chewable, these shapes leave no solid residue in the mouth.

The gelatin used in the delivery system of the present invention can generally be selected from a wide variety of gelatins having a Bloom value of 100–375. A 250 Bloom grade of gelatin is preferred, although not especially critical to the practice of this invention.

The term "gelatin" as used herein refers to a heterogenous mixture of water-soluble proteins of high average molecular weight derived from collagen by hydrolytic action. Gelatin is strongly hydrophilic, absorbing up to ten times its weight of water and forming reversible gels of high strength and viscosity. It is preferable that a thermo-reversible gelatin be used to aid in providing a homogenous mixture.

Gelatin is employed in the delivery system of the present invention in an amount from about 2 to about 50% by weight of the gummy delivery system of the present invention, preferably from about 5% to about 30% by weight.

After the gelatin is dissolved, preferably completely dissolved, in a minimum amount of water, its structure is modified by incorporating glycerin and heating the resulting mixture in a specific temperature range. Glycerin is a clear, colorless, odorless, syrup liquid which has a high boiling point of 290° C. and is soluble in water. The glycerin useful for the present invention can be obtained from numerous commercial sources such as Penta Corporation and is most preferably dehydrated to over about 99% purity. Nevertheless, the water content of glycerin is not critical. Glycerin is provided in an amount preferably from about double to quadruple the amount of gelatin by weight, and even more preferably from about double to triple by weight In the gummy delivery system of the present invention the ratio of gelatin to glycerin can be as high as about 1:1, but preferably the ratio is from about 0.20 to about 0.34 of gelatin to glycerin.

Water comprises a part of the inventive system in an amount from about 0% to about 20% by weight, more preferably less than about 5%, and most preferably in an amount of 0% of gummy delivery system of the invention. This is especially surprising since most delivery systems require the presence of at least some moisture in the final composition. It is important for the formation of the glycerylated gelatin matrix of the invention that after the aqueous gelatin solution is mixed with glycerin, the resulting mixture is heated in a controlled range to reduce the initial moisture content from about 10% to about 80%, and most preferably about 100%, by weight of the glycerylated gelatin matrix. The glycerylated gelatin matrix of the present invention is obtained as a direct result of the reduction in moisture content by controlling the temperature from about 85° C. to just below 100° C.

The glycerylated gelatin matrix is a solid material which has a gummy consistency similar to that of a gummy bear confection. It is a continuous solid, readily soluble in aqueous solutions and is entirely consumable, namely, it leaves no residue in the mouth upon chewing. The glycerylated gelatin matrix of the present invention can be pulled and stretched. While not bound by theory, empirical evidence indicates crosslinking in the glycerylated gelatin matrix of the invention. It is believed that the structure of the matrix is polymeric. It is also believed that the characteristics of gumminess, long texture, lay flat, elasticity evidenced by bouncing back upon prolonged mastication, are all due to the polymeric nature of the glycerylated gelatin matrix.

Gumminess is a mechanical masticatory property of the texture of the glycerylated gelatin matrix of the present invention. It can be defined in terms of cohesiveness, and hardness of the glycerylated gelatin matrix. Other textural characteristics of a gummy consistency also include elasticity which permits the glycerylated gelatin to recover its shape upon mastication many times before it is finally consumed.

A matrix having gummy consistency is also viscous, having a viscosity from about 1000 cps to about 100,000 cps at a given temperature.

The term "active" means an active ingredient which can be selected from one or more drugs, flavors and sweeteners.

The term "drug" when used to classify the active includes medicaments, vitamins, mineral supplements and other chemical or biological substances intended for use in the treatment, prevention, diagnosis, cure or mitigation of disease or illness, or substances which affect the structure or function of the body. Mixtures of drugs are operable.

Suitable categories of drugs that may be delivered from the glycerylated gelatin matrix of the invention vary widely and generally represent any stable drug combination. Illustrative categories and specific examples include:

(a) Antitussives, such as dextromethorphan, dextromethorphan hydrobromide, noscapine, carbetapentane citrate, and chlophedianol hydrochloride;

(b) Antihistamines, such as chlorpheniramine maleate, phenindamine tartrate, pyrilamine maleate, doxylamine succinate, and phenyltoloxamine citrate;

(c) Decongestants, such as phenylephrine hydrochloride, phenylpropanolamine hydrochloride, pseudoephedrine, hydrochloride ephedrine;

(d) Various alkaloids, such as codeine phosphate, codeine sulfate and morphine;

(e) Mineral supplements such as potassium chloride and calcium carbonates, magnesium oxide and other alkali metal and alkaline earth metal salts;

(f) Laxatives, vitamins and antacids;

(g) Ion exchange resins such as cholestyramine;

(h) Anti-cholesterolemic and acid-lipid agents such as gemfibrozil;

(I) Antiarrhythmics such as N-acetyl-procainamide;

(j) Antipyretics such as acetaminophen, aspirin and ibuprofen;

(k) Appetite suppressants such as phenylpropanolamine hydrochloride or caffeine;

(l) Expectorants such as guaifenesin;

(m) Hormones, antibodies, antigens and other bioagents; and (n) Stop-smoking and anti-craving ingredients such as nicotine.

Additional useful active medicaments include antiinflammatory substances, coronary dilators, cerebral dilators, peripheral vasodilators, anti-infectives, psychotropics, antimanics, stimulants, gastrointestinal sedatives, antidiarrheal preparations, antianginal drugs, vasodilators, antihypertensive drugs, vasoconstrictors and migraine treatments, antibiotics, tranquilizers, antiphychotics, antitumor drugs, anticoagulants and antithrombotic drugs, hypnotics, sedatives, antiemetics, antinauseants, anticonvulsants, neuromuscular drugs, hyper- and hypoglycaemic agents, thyroid and antithyroid preparations, diuretics, antispasmodics, uterine relaxants, nutritional additives, antiobesity drugs, anabolic drugs, erythropoietic drugs, antiasthmatics, cough suppressants, mucolytics, antiuricemic drugs, and the like.

Preferred drugs are calcium carbonate, and cough and cold formulations known to the skilled artisan.

Flavors may be chosen from natural and synthetic flavoring agents. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, grape, lime and grapefruit and fruit essences including apple, pear, peach, grape, strawberry, raspberry, cherry, plum, pineapple, apricot or other fruit flavors.

Representative flavor oils include spearmint oil, peppermint oil, cinnamon oil, and oil of wintergreen (methylsalicylate). Also useful are artificial, natural or synthetic fruit flavors such as citrus oils including lemon, orange, grape, lime and grapefruit, and fruit essences including apple, strawberry, cherry, pineapple and so forth.

Examples of citrus or fruit oils and/or essences which are useful include a host of materials such as apple, apricot, banana, blueberry, cherry, grape, grapefruit, lemon, lime, orange, pear, peaches, pineapple, plum, raspberry, strawberry and the like. Mixtures and derivatives of these materials are contemplated.

Clove oil, bay oil, anise oil, eucalyptus oil, thyme oil, cedar leaf oil, oil of nutmeg, oil of sage, oil of bitter almonds and cassia oil can also be used. Commonly used flavors include menthol, artificial vanilla, cinnamon derivatives, and various fruit flavors, whether employed individually or in admixture.

Flavorings such as aldehydes and esters including cinnamyl acetate, cinnamaldehyde, citral diethylacetal, dihydrocarvyl acetate, eugenyl formate, p-methylamisol, and so forth may also be used.

Further examples of aldehyde flavorings include, but are not limited to acetaldehyde (apple); benzaldehyde (cherry, almond), anisic aldehyde (licorice, anise); cinnamic aldehyde (cinnamon); citral, i.e., alpha citral (lemon, lime); ethyl vanillin (vanilla, cream); hellotropine, i.e., piperonal (vanilla, cream); vanillin (vanilla, cream); alpha-amyl cinnamaldehyde (spicy fruity flavors); butyraldehyde (butter, cheese); valcraldehyde (butter, cheese); citronellal; decannal (citrus fruits); aldehyde C-8 (citrus fruits); aldehyde C-9 citrus fruits); aldehyde C-12 (citrus fruits); 2-ethylbutyraldehyde (berry fruits); tolyl aldehyde (cherry, almond); veratraldehyde (vanilla); 2,6-dimethyl-5-heptenal, i.e., melonal (melon); 2,6-dimethyloctanal (green fruit); and 2-dodecenal (citrus, mandarin), mixtures thereof and the like.

Other specific flavor compounds such as ethylacetate, thiophene, ethylpropionate, ethyl butyrate, 2-hexanoate, 2-methylpyazine, heptaldehyde, 2-octanone, limonene, and eugenol are also useful.

The active ingredients content (drugs, flavors, sweeteners, etc. heretofore described) of the present delivery systems is generally in the range of about 0.02% to about 40% by weight of the delivery system. Preferably, the actives are present in amounts of about 0.5% to about 30% by weight of the delivery system and most preferably about 2% to about 12%. Those skilled in the art may optimize the quantity of actives present, depending upon the particular compound or combination thereof which is utilized.

The inventive delivery systems of the present invention can optionally include additional food grade quality of conventional additives which can be admixed with the glycerylated gelatin matrix of the present invention. Representative additives include oleaginous materials, medium chain triglycerides, flours, sweeteners, colorings, humectants, fillers, emulsifiers, thickeners and mixtures thereof. Any one or more of the foregoing additional food grade additives may be admixed with the gelatin matrix so as to comprise from about 0.01% to about 50% by weight, or even more, of the delivery system.

In a preferred embodiment the glycerylated gelatin matrix is admixed with oleaginous material. It has been unexpectedly found that the addition of oleaginous materials, preferably solid oleaginous materials at room temperature, can speed up the formation of a solid gummy delivery system. The oleaginous material can be a conventional edible glyceride, fat or oil. In general, the oleaginous component is an animal fat such as tallow, lard, hydrogenated animal and/or vegetable oils, which are solids at room temperature. Paramount B and Durem 117 as provided by Van Den Bergh company are examples of hard fats useful in the present invention.

The medium chain triglycerides of the present invention are selected from mono-, di- and polyhydric esters of a fatty acid, as well as mixtures thereof. Those fatty acids useful in forming the medium chain triglyceride have from 6 to 12 carbon atoms in the fatty acid chain. Non-limiting examples of fatty acids of this type are caprylic acid, capric acid, linoleic acid, capric acid, lauric acid, succinic acid and mixtures thereof. Preferably the medium chain triglyceride is the glycerol ester of these acids.

Specific examples of medium chain triglycerides useful in the present invention include those sold under the MIGLYOL® trademark by Huls Aktiengesellschaft. There are various neutral, medium chain triglyceride oils marketed under the MIGLYOL® brand. For example: MYGLYOL® 810 is a medium chain triglyceride of fractionated $C_8$–$C_{10}$ coconut oil fatty acids and is classified as a caprylic/capric triglyceride. It has a higher caprylic acid content and a correspondingly lower capric acid content that MIGLYOL® 812, which is also a caprylic/capric triglyceride. MIGLYOL® 818 is a triglyceride of fractionated $C_8$–$C_{10}$ coconut oil fatty acids with a 5% portion of linoleic acid. It is classified as a caprylic/capric/linoleic triglyceride. MIGLYOL® 829 is a glyceryl ester of fractionated $C_8$–$C_{10}$ coconut oil fatty acids linked to succinic acid. It is classified as a caprylic/capric/diglyceryl succinate triglyceride. MIGLYOL® 840 is a propylene glycol diester of saturated vegetable fatty acids with $C_8$–$C_{10}$ chain-lengths and is classified as a propylene/glycol/dicaprylate/dicaprate triglyceride.

In addition to the MIGLYOL® brand of medium chain triglyceride oils, other brands such as NEOBEE® M-5, a caprylic/capric triglyceride from Stepan Company, Maywood, N.J., and DIGEST™ 65, a medium chain triglyceride prepared from edible vegetable oil and having a minimum of 65% $C_8$ esters present, and have been found to be useful.

As previously pointed out, medium chain triglycerides have been used as stable lipid solvents for colors, flavors, vitamins, antioxidants, and pharmaceuticals. These low viscosity oils have also been used in confectionery products as anti-sticking and lubricating agents and for dust prevention for spices, seasonings and other dry mixes.

The preferred medium chain triglycerides of the present invention include the fractionated $C_8$–$C_{10}$ coconut oil fatty acids classified as caprylic/capric triglycerides.

The present invention encompasses the inclusion of both natural and artificial sweeteners. The sweeteners may be chosen from the following non-limiting list: sugars such as sucrose, glucose (corn syrup), dextrose, invert sugar, fructose, and mixtures thereof; saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof.

Other conventional additives which are useful in the gummy delivery systems of the present invention include mineral adjuvants such as calcium carbonate, magnesium carbonate, alumina, aluminum hydroxide, aluminum silicate, talc, tricalcium phosphate and the like; as well as mixtures thereof. These mineral adjuvants may also serve as fillers and texturizing agents.

Emulsifiers such as lecithin, glycerol monostearate, fatty acid monoglycerides, diglycerides and triglycerides, glycerol triacetate, propylene glycol monostearate and mixtures thereof can also be included in the gummy delivery system of the present invention.

Thickeners useful for the delivery systems of the present invention include pectin, food gums, hydroxyethyl cellulose, hydroxypropyl methyl cellulose and carboxymethyl cellulose.

In a preferred embodiment, the actives are released from a shearform matrix carrier prepared by flash-flow processing a feedstock which includes an active and a carrier material.

The term "flash flow" has become recognized in the art as referring to the conditions of temperature and force required to transform a solid feedstock having a certain morphological and/or chemical structure to a new solid having a different morphological and/or chemical structure without subjecting the solids to heat history or other requirements inherent in extrusion processing. The term "flash flow" is described in co-owned U.S. Pat. No. 5,236,734, issued Aug. 17, 1993 and U.S. Pat. No. 5,238,696, issued Aug. 24, 1993, U.S. Pat. No. 5,380,473 issued Jan. 10, 1995, U.S. Pat. No. 5,518,730 issued May 21, 1996, U.S. Pat. No. 5,387,431 issued Feb. 7, 1995, as well as U.S. Pat. No. 5,597,608, the complete disclosures of which are incorporated herein by reference.

The term "flash flow" refers to subjecting an appropriate feedstock to conditions of temperature and force which induce a solid feedstock to undergo rapidly such physical and/or chemical transformation. The time during which the feedstock material is subjected to elevated temperatures is very short. Flash flow processing can be accomplished either by a flash heat method or a flash shear method, as described further herein. In the flash heat method, the material subjected to temperature for generally only tenths of a second, whereas in the flash shear method the material is subjected to temperatures for a time on the order of seconds.

In the flash heat process, a shearform matrix can be formed by spinning a feedstock in a "cotton candy" fabricating type machine. The spinning machine used to achieve a flash heat process can be a cotton candy type machine, such as the EconoFloss Model 3017, manufactured by Gold Metal Products Company of Cincinnati, Ohio, a machine having a coiled heater element as disclosed in U.S. Pat. No. 5,427,811 issued Jun. 27, 1995, herein incorporated by reference, and the like. It will be appreciated by those skilled in the art that any apparatus or physical process which provides similar forces and temperature gradient conditions can also be used. For simplicity in disclosing and describing this invention, the term flash heat will be understood to mean a process which includes subjecting a feedstock to the combination of temperature, thermogradients, flow, flow rates, mechanical forces of the type produced in a candy machine or the above-referenced U.S. Pat. No. 5,427,811, as well as other apparatus having a spinning head, such as that described in U.S. Pat. Nos. 5,445,769, 5,447,423 and 5,458,823 (incorporated herein by reference). The apparatus is operated at the temperature and speed which permits flash heat of the feedstock with deterioration of any of its ingredients.

In the flash heat process, the feedstock material is heated sufficiently to create an internal flow condition, i.e., intraparticle flow, which permits part of the feedstock to move at a subparticle level with respect to the rest of the mass and exit openings provided in the perimeter of the spinning head. The centrifugal force created in the spinning head flings the flowing feedstock material outwardly from the head so that it reforms with a changed structure. The force required to discharge flowable feedstock is provided by the forces which result from the spinning head. The flash heat process has been used to produce an amorphous matrix from a crystalline material, as disclosed in the aforementioned Fuisz patents.

In the flash shear process, a shearform matrix is formed by raising the temperature of the feedstock material, which includes a non-solubilized component, to a point where said component undergoes intraparticle flow. The non-solubilized component is preferably a saccharide based carrier material which is solid at about room temperature.

The feedstock is advanced and ejected from an extruder or similar type of machinery while the carrier material is undergoing intraparticle flow, and is then subjected to disruptive fluid shear forces to form multiple parts or masses which have a morphology different from that of the original feedstock and which comprise the active.

The flash shear process can be carried out in an apparatus which has means for increasing the temperature of a non-solubilized feedstock and means simultaneously advancing it for ejection. A multiple heating zone twin extruder can be used for increasing the temperature and advancing feedstock. The apparatus includes a means for ejecting the feedstock in a condition for shearing it to provide the shearform matrix. The means for ejecting is in fluid communication with the means for increasing the temperature and is arranged at the point to receive the feedstock while it is in the internal flow condition. The means for ejecting the feedstock is preferably a nozzle which provides sufficient frictional gas force applied to the ejected feedstock stream to disrupt the stream and form and maintain a solloid.

Apparatus for flash shear processing of the feedstock is described in co-pending U.S. Pat. No. 5,380,473 issued Jan. 10, 1995 which is incorporated herein by reference. The means for shearing is arranged proximally to the ejector and is disposed to effect the shear of the feedstock while it is in the internal flow condition. Preferably, the means for shearing is the means for delivering fluid such as air at sufficient velocity and at elevated temperature against the feedstock stream as it exits from a nozzle. Such a device can be an external atomizing nozzle. The means for shearing can also be a chamber in which the environment can be maintained to induce shear upon the collision of a high velocity of a stream of feedstock directed against a preselected and maintained environment.

The carrier materials included in the shearform matrix are preferably saccharide-based and/or water-soluble cellulosic materials or mixtures thereof. A non-limiting list of suitable saccharide carriers include sucrose, lactose, fructose, dextrose, sorbitol, manitol, maltose, synthetically-derived saccharide materials such as polydextrose, and the like and mixtures thereof. Alternative saccharide materials such as maltodextrins and/or corn syrup solids are also useful. Suitable water-soluble cellulosic materials include methylcellulose, ethylcellulose, hydroxymethyl or ethylcellulose, alkali-metal salts of carboxymethylcelluloses and the like and mixtures thereof.

The saccharide-based carrier material can also be processed with additional ingredients. Such additives are primarily related to the texture and do not detract from the appearance or utility of the matrix as a delivery system for an active ingredient. Examples of useful additives which were previously discussed include fats, medium chain triglycerides, sweeteners, flavors, colorings, humectants, fillers, emulsifiers, thickeners and the like.

In an embodiment of the present invention, the shearform matrix carrier bears no active ingredient and is used as a filler when admixed with the elastic, continuous glycerylated gelatin matrix of the present invention.

In a preferred embodiment of the present invention, active ingredients are released from the shearform matrix carrier. The active is admixed with a carrier material component and then subjected to flash flow conditions thereby forming a shearform matrix carrier which when admixed with the glycerylated gelatin matrix of the present invention forms a solid, gummy delivery system. The resulting product is an elastic, water soluble, gummy delivery system which is entirely consumable in the mouth and which provides an efficient way for the steady delivery of an active to the mouth cavity.

In another preferred embodiment, a carrier material component is admixed with gelatin and then subjected to flash flow conditions as defined hereinabove. The resulting shearform gelatin matrix wetted very quickly in water but shows delayed hydration due to the fact that gelatin matrix has to release from the fused layer of the carrier material, and it takes time to dissolve the fused carrier material. While the carrier material and the gelatin may be admixed in many proportions, a preferred ratio is 30% gelatin to 70% carrier material component. The aqueous solution of shearform gelatin matrix may then be admixed with glycerin and an active ingredient to form the gummy, elastic and entirely consumable delivery system of the present invention. In this embodiment, as well, the active ingredient may also be in the form of a shearform matrix as a result of "flash-flow" processing. The weight percentages of the foregoing ingredients will preferably be within the ranges heretofore described.

A preferred saccharide-based carrier material useful in the practice of the present invention is referred to herein as maltodextrin. Maltodextrins contain a mix of sugars and polysaccharides which range from long-chain oligomers resulting from starch hydrolysis to sugars having a low number of monomeric units. Under FDA guidelines maltodextrin consists of nonsweet, nutritive saccharide polymers having a D.E. of less than 20, while corn syrup solids is regarded by the FDA as having a D.E. greater than 20. The present inventor, however, refers to maltodextrins collectively as solid saccharide-based material consisting of nonsweet, nutritive saccharide polymers and other oligomers having six-carbon monomer units which collectively provide a carrier material capable of forming a matrix including maltodextrins having a D.E. of up to 45.

Maltodextrins have been used as a nonfat additive. One of the greatest advantages of maltodextrins is that they do not act adversely on the intestinal tract. Consequently, they are particularly useful as a bulking agent and as a fat substitute. Moreover, maltodextrins are generally recognized as safe (GRAS) by the United States Food and Drug Administration.

Unfortunately, the ability to disperse maltodextrins and use them in different products is limited by their physical and chemical cohesiveness. They are unlike their high sugar counterparts in that they are relatively unreactive and physically resistive to mixing and dispersing. While artisans have been able to process sugar to enhance its utility in food and medicaments, the maltodextrins do not appear to be as versatile. Commonly owned U.S. Pat. Nos. 5,387,431 and 5,597,608 are directed to flash-flow processing of maltodextrin and oleaginous material.

The maltodextrins useful as carriers in the present invention are those mixtures resulting from hydrolysis as described above which have a D.E. of up to 45. The higher D.E. solid maltodextrins are within the scope of the present invention. Maltodextrins which are useful in the present invention include some products which are sold under the trademark MALTRIN®, a product of the Grain Processing Corporation of Muscatine, Iowa.

EXAMPLES

The following examples serve to provide further appreciation of the invention, but are not meant in any way to restrict the effective scope of the invention. Unless indicated otherwise, the examples were carried out in a three inch diameter cable heater flash-flow apparatus of the type described in U.S. Pat. No. 5,427,811 issued Jun. 27, 1995, the disclosure of which is incorporated herein by reference. All materials used in the examples set forth below are readily commercially available.

Example 1
Glycerylated Gelatin Matrix

A glycerylated gelatin matrix was prepared by dissolving gelatin in water and adding glycerin to the aqueous gelatin solution in the quantities set forth in Table 1. The resulting mixture was heated from about 85° C. to just below 100° C. in order to remove a portion of the water. A gummy, continuous glycerylated gelatin matrix was formed.

Example 2
Antacid Formulations

Nine different antacid formulations were prepared containing the glycerylated gelatin matrix of the present invention as prepared in Example 1 above. The composition of each formulation has been summarized in Table 1 hereinbelow.

The glycerylated gelatin matrix prepared in Example 1 was then admixed with all remaining ingredients, namely calcium carbonate, the antacid active, and other conventional additives. The texture of the resulting delivery systems was gummy and could bounce back upon prolonged mastication. In some cases, the delivery systems became stickier if glycerin or fat were removed. The samples which evidenced the best degree of gumminess, contained corn syrup solids.

Example 3

Cough and Cold Formulations

Two different cough and cold formulations were prepared containing the glycerylated gelatin matrix of the present invention. The composition of these formulations is summarized in Table 2 below.

A gelatin solution was prepared by dissolving gelatin in water. Glycerin was added to the gelatin solution. The resulting mixture was heated from about 85° C. to just below 100° C. to remove about 7% of the water. A gummy, continuous glycerylated gelatin matrix was formed.

Separately, a mixture of sucrose, menthol, eucalyptus oil and corn syrup solids 36DE in the amounts shown in Table 2 were added to the glycerylated gelatin matrix. A gummy, continuous, elastic delivery system for a cough and cold medication was obtained.

TABLE I

ANTACID FORMULATIONS

| SAMPLES | GELATIN** TYPE B TEXTURES | GLYCERIN | SOLID FAT | WATER (Final)*** | FLAVOR | CaCO₃ | ARTIFICIAL | CORN SWEETENER SOLIDS 36DE | CORN SYRUP SOLIDS 42DE | WHEY SYRUP |
|---|---|---|---|---|---|---|---|---|---|---|
| 1 | 4.00 | 12.83 | 4.33 | 12.83 (12.08) | 0.70 | 31.25 | 0.1995 | — | 33.86 | — |
| 2 | 4.00 | — | 4.33 | 12.83 (12.00) | 0.70 | 31.25 | 0.1995 | 46.69 | — | — |
| 3 | 4.00 | 12.83 | — | 20.00 (12.00) | 0.70 | 31.25 | 0.1995 | 26.69 | — | — |
| 4 | 4.00 | 12.83 | 4.33 | 12.83 (12.00) | 0.70 | 31.25 | 0.1995 | — | — | — |
| 5 | 4.00 | 12.83 | 4.33 | 12.83 (12.00) | 0.70 | 31.25 | 0.1995 | — | 19.23 | 3.33 |
| 7 | 4.00 | 12.83 | 4.33 | 11.48 (12.00) | 0.70 | 31.25 | 0.1995 | — | 33.87 | — |
| 8 | 4.00 | 12.83 | — | 12.83 (12.00) | 0.70 | 31.25 | 0.1995 | 38.19 | — | — |
| 9 | 4.00 | 12.83 | 4.33 | 12.83 | 0.70 | 31.25 | 0.1995 | — | 25.56 (12.00) | 5.00 |

| SAMPLES | SUGAR 6X PROTEIN | VITAMINS DOMINO | ATTRIBUTES 45% RDA |
|---|---|---|---|
| 1 | — | | gummy |
| 2 | — | | sticky |
| 3 | — | | sticky |
| 4 | 33.86 | | gummy |
| 5 | — | 40.15 | gummy |
| 6 | — | | gummy |
| 7 | — | | hard |
| 8 | — | | sticky |
| 9 | — | 40.15 | gummy |

*Shearform Matrix is absent
**All ingredients are expressed in weight %
***Final water concentration is the concentration of water in the glycerylated gelatin matrix.

TABLE 2

COUGH AND COLD FORMULATIONS

| SAMPLES | GELATIN TYPE B | GLYCERIN | SUCROSE | WATER INITIAL | WATER FINAL | MENTHOL/ EUCALYPTUS OIL | CORN SYRUP SOLIDS 36DE | ATTRIBUTES TEXTURE |
|---|---|---|---|---|---|---|---|---|
| 1* | 7.00 | 22.60 | 27.00 | 16.25 | 15.00 | 0.37 | 27.00 | Gummy |
| 2* | 10.50 | 28.25 | 27.00 | 7.10 | 6.30 | 0.37 | 27.00 | Sticky |

*No shearform matrix is present. All ingredients are in % weight

Example 4
Antacid Formulation

In this example, an antacid formulation was prepared using the ingredients set forth in Table 3 below

TABLE 3

Antacid Formulation

| Ingredients | Weight % |
|---|---|
| Gelatin Type B 250 Bloom | 4.00 |
| Glycerin (99%) | 12.83 |
| Water | |
| Initial | 12.83 |
| Final | 12.00 |
| Corn Syrup Solids DE42 | 6.64 |
| Solid Fat | 3.00 |
| Flavor | 0.70 |
| Shearform Matrix | 60.00 |

A gelatin solution was prepared by dissolving gelatin in water. Glycerine was added to the gelatin solution. The resulting mixture was heated from about 85° C. to just below 100° C. in order to remove most of the water, such that only from about 8% to about 15% of the initial water content remained. A gummy, continuous glycerated gelatin matrix was formed.

TABLE 4

Shearform Matrix Encapsulating Antacid

| Ingredients | Weight (g) |
|---|---|
| CaCO$_3$ | 36.00 |
| Corn Syrup Solids DE42 | 22.62 |
| Solid Fat | 1.20 |
| Artificial Sweetener | 0.55 |

Separately, a mixture of calcium carbonate, solid fat, artificial sweetener, such as aspartame and acesulfame K, and corn syrup solids DE42 in amounts shown in Table 4 were admixed and subjected to flash flow conditions to form a shearform matrix. About 60% of the resulting shearform matrix was admixed with all the ingredients set forth in Table 3. A gummy elastic solid material was formed which was used with excellent results to deliver an antacid active such as calcium carbonate. The gummy solid material had lay-flat memory and could be masticated over a long period of time thereby ensuring a uniform delivery of the antacid.

Example 5
Cough and Cold Formulation

In this example, a cough and cold formulation was prepared using ingredients set forth in Table 5 below:

TABLE 5

Cough and Cold Formulation

| Ingredients | Weight % |
|---|---|
| Gelatin Type B 250 Bloom | 10.50 |
| Glycerin (99%) | 30.00 |
| Water Initial | 7.10 |
| Water Final | 3.20 |
| Sucrose | 27.00 |
| Corn Syrup Solid 42 DE | 20.40 |
| Solid Fat | 3.00 |
| Flavor | 0.20 |
| Shearform Matrix Encapsulating Menthol from Table 6 | 1.25 |

A gelatin solution was prepared by dissolving gelatin in water. Glycerin was added to the gelatin solution. The resulting mixture was heated from about 85° C. to just below 100° C. to remove about 50% or less of the water. A gummy, continuous glycerylated gelatin matrix was formed.

TABLE 6

Shearform Matrix Encapsulating Menthol

| Ingredients | Weight % |
|---|---|
| Stearine | 48.5 |
| HPMC* | 12.0 |
| Flavor | 1.5 |
| MCT**-Oil | 2.0 |
| Menthol/Eucalyptus | 36.0 |

*Hydroxy Propyl Methyl Cellulose.
**Medium Chain Triglyceride

Separately, a mixture of stearine, HPMC, flavors, such as capsicum oleoresin and citric acid, MCT-oil, methyl and eucalyptus in the amounts shown in Table 6 above, were added to corn syrup solids DE42 in a ratio of 1:1 to form a feedstock which was subjected to flash-flow processing to form a shearform matrix. Flash-flow processing was accomplished by spinning in a flash-heat apparatus operated at 3500 r.p.m. to produce a shearform matrix according to the method disclosed in U.S. Pat. No. 5,429,836, incorporated herein by reference. The resulting matrix was then admixed with the glycerated gelatin, sucrose, corn syrup solids 42E and solid fat in the amounts shown in Table 5. A solid product was obtained which was gummy, elastic and entirely consumable in the mouth. The gummy composition remained stable and could be masticated over a long period of time to deliver the menthol and eucalyptus cough and cold formula over a long period of time, approximately 45 minutes.

Example 6
Cough and Cold Formulation

Seven different cough and cold formulations were prepared based on the consumable, gummy delivery system of the present invention. The glycerylated gelatin matrix of the present invention was admixed with an active ingredient released from a shearform matrix carrier prepared by subjecting to flash-flow conditions a feedstock comprising the active ingredient as illustrated in Table 7 below.

Encapsulated menthol was prepared by subjecting a feedstock having the ingredients set forth in Table 8 to flash flow conditions provided by an Econo Floss machine having a Jefferson head spinning at 22.5% duty cycle. The feedstock was prepared by first admixing lecithin and a flavor such as capsicum oleoresin with menthol crystals dissolved into MCT oil. A molten emulsifier such as Dimoden LSK was added to the initial mixture. Subsequently, polydextrose, cornstarch, HPMC, sorbitol and calcium carbonate were also added to the resulting mixture to form a feedstock which was

TABLE 7

COUGH AND COLD FORMULATIONS

| SAMPLES | GELATIN TYPE B | GLYCERIN | SUCROSE | WATER INITIAL | WATER FINAL | MENTHOL*/ EUCALYPTUS OIL* | CORN SYRUP SOLIDS 42DE | ENCAP* MENTHOL |
|---|---|---|---|---|---|---|---|---|
| 1 | 10.50 | 28.25 | 27.00 | 7.10 | 6.40 | 0.17 | 22.54 | 4.44 |
| 2 | 10.50 | 28.25 | 27.00 | 7.10 | 6.40 | 0.36 | 16.79 | 10.00 |
| 3 | 10.50 | 28.25 | 27.00 | 7.10 | 6.30 | — | 17.15 | — |
| 4 | 10.50 | 30.00 | 27.00 | 7.10 | 6.40 | — | 22.90 | — |
| 5 | 10.50 | 30.00 | 27.00 | 7.10 | 6.40 | 0.45 | 19.95 | — |
| 6 | 10.50 | 30.00 | 27.00 | 7.10 | 6.40 | 0.45 | 23.70 | — |

| SAMPLES | ENCAP* MENTHOL TABLE 8 | ENCAP* MENTHOL TABLE 9 | ATTRIBUTES TEXTURE TABLE 10 |
|---|---|---|---|
| 1 | — | — | STICKY |
| 2 | — | — | SHORT BITE |
| 3 | 10.0 | — | STICKY |
| 4 | — | 2.50 | STICKY |
| 5 | 5.00 | — | STICKY |
| 6 | — | 1.25 | STICKY |

All ingredients are in % weight
*Shearform matrix components.

In all these examples, menthol was released from a first shearform matrix as set forth in Tables 8, 9 and 10. As a result, the menthol active is released from a double encapsulation, i.e., as part of an initial shearform matrix which is subsequently added as a component of a second shearform matrix where other ingredients including corn syrup solids are present.

The texture of the resulting cough and cold delivery systems was generally sticky. Upon increasing the content of encapsulated menthol, the resulting delivery system had a short bite, i.e., it broke off easily. This was due to the nature of the combined carrier materials.

Tables 8, 9 and 10 below list the ingredients present in preparing different shearform matrices for menthol and eucalyptus encapsulation.

TABLE 8

Shearform Matrix Encapsulating Menthol (66F)

| Ingredients | Weight % |
|---|---|
| MCT* Oil | 7.50 |
| Menthol Crystals | 7.50 |
| Lecithin | 0.50 |
| Flavor | 0.15 |
| Emulsifier | 7.50 |
| Polydextrose | 27.35 |
| Corn Starch | 10.00 |
| HPMC** | 16.00 |
| Sorbitol | 6.00 |
| CaCO$_3$ | 10.00 |
| Zinc Gluconate Powder | 7.50 |

*Medium Chain Triglyceride
**Hydroxy Propyl Methyl Cellulose subjected to flash flow processing. The resulting shearform matrix bearing menthol was utilized as an ingredient of cold and cough formulations 1 and 2 as set forth in Table 7.

TABLE 9

Shearform Matrix Encapsulating Menthol (MPD-04)

| Ingredients | Weight % |
|---|---|
| Stearine | 63.80 |
| HPMC | 14.00 |
| Flavor | 0.20 |
| MCT Oil | 4.00 |
| Menthol/Eucalyptus | 18.00 |

The above ingredients as set forth in Table 9 were admixed with polydextrose in a ratio of 1:1 and subjected to flash flow conditions to form a menthol bearing shearform matrix which was subsequently utilized as an ingredient of cold and cough formulations 3 and 5 of Table 7.

TABLE 10

Shearform Matrix Encapsulating Menthol (MEE07C)

| Ingredients | Weight % |
|---|---|
| Stearine | 24.25 |
| HPMC | 6.00 |
| Flavor | 0.25 |
| MCT Oil | 1.00 |
| Citric Acid | 0.50 |
| Menthol/Eucalyptus | 18.00 |
| Corn Syrup Solid 36DE | 50.00 |

The above ingredients as set forth in Table 10 were subjected to flash flow conditions to form a menthol bearing shearform matrix which was used as an ingredient of the cold and cough formulations 4 and 6 of Table 7.

Example 7

In this example, a glycerylated gelatin matrix was prepared by utilizing a gelatin bearing shearform matrix formed by using the ingredients listed in Table 11 below.

TABLE 11

Shearform Gelatin Matrix

| Ingredients | Weight % |
| --- | --- |
| Gelatin | 30.00 |
| Fructose Powder | 10.00 |
| Sugar 6X Powder | 30.00 |
| Corn Syrup Solids 42DE | 30.00 |

The above ingredients were admixed and then subjected to flash-flow processing by spinning in a flash-heat apparatus operated at 75–105° C. and 3500 r.p.m. to produce a shearform matrix.

The resulting gelatin matrix is then dissolved in water to form an aqueous gelatin solution. Glycerin in an amount of about 30 weight % is added to about 15 weight % aqueous gelatin solution and the resulting mixture is heated from about 85° C. to just below 100° C. to remove about 50% or the entire amount of moisture. A gummy, continuous glycerylated matrix is formed which upon admixing with an active forms a gummy, elastic, solid product which is entirely consumable in the oral cavity. The glycerylated gelatin matrix obtained in this example is highly effective in combination with actives either by themselves or released from a shearform matrix carrier as in Examples 3, 4 and 5, above.

Example 8

A glycerylated gelatin matrix is prepared by dissolving gelatin in water and adding glycerin to the aqueous gelatin solution in the quantities set forth in Table 1. The resulting mixture is heated from about 85° C. to just below 100° C. in order to remove substantially all of the water. An elastic continuous glycerylated gelatin matrix is formed which combines well with various actives to yield a consumable delivery system.

What is claimed is:

1. A consumable, gummy delivery system which comprises:

an elastic, continuous glycerylated gelatin matrix prepared by heating an aqueous solution of gelatin admixed with glycerin to a temperature and for a time sufficient to remove about 100% by weight of initial moisture content to provide a gummy glycerylated gelatin matrix as an elastic, water soluble solid; and one or more active ingredients in the form of a shearform matrix admixed with said glycerylated gelatin matrix, whereby said consumable gummy deliver system is formed which is readily soluble in aqueous media; wherein said results glycerylated gelatin matrix contains about 0% moisture.

2. A consumable, gummy delivery system which comprises:

an elastic, continuous glycerylated gelatin matrix prepared by heating an aqueous solution of gelatin admixed with glycerin to a temperature and for a time sufficient to remove from about 10% to about 100% by weight of initial moisture content to provide a gummy glycerylated gelatin matrix as an elastic, water soluble solid; and one or more active ingredients in the form of a shearform matrix admixed with said glycerylated gelatin matrix, whereby said consumable gummy delivery system is formed which is readily soluble in aqueous media; wherein said glycerine is present in an amount of from about 10% by weight to about 50% by weight of said gummy delivery system.

3. A consumable, gummy delivery system which comprises:

an elastic, continuous glycerylated gelatin matrix prepared by heating an aqueous solution of gelatin admixed with glycerin to a temperature and for a time sufficient to remove about 100% by weight of initial moisture content to provide a gummy glycerylated gelatin matrix as an elastic, water soluble solid; and one or more active ingredients in the form of a shearform matrix admixed with said glycerylated gelatin matrix, whereby said consumable gummy delivery system is formed which is readily soluble in aqueous media; wherein said glycerylated gelatin matrix contains residual moisture in an amount of about 0% by weight of said matrix.

4. A consumable, gummy delivery system which comprises:

an elastic, continuous glycerylated gelatin matrix prepared by heating an aqueous solution of gelatin admixed with glycerin to a temperature and for a time sufficient to remove from about 10% to about 100% by weight of initial moisture content to provide a gummy glycerylated gelatin matrix as an elastic, water soluble solid; and one or more active ingredients provided as a component of a shearform matrix carrier prepared by flash-flow processing a feedstock comprising said active ingredient and a carrier material, said processed active ingredient being further admixed with said glycerylated gelatin matrix, whereby said consumable gummy delivery system is formed which is readily soluble in aqueous media; and wherein said active ingredient is selected from the group consisting of medicaments, flavors, sweeteners and mixtures thereof.

5. The delivery system of claim 4, wherein said carrier material is selected from the group consisting of saccharides, water soluble cellulosics and mixtures thereof.

6. The delivery system of claim 5, wherein said saccharide is corn syrup solids.

7. The delivery system of claim 4, wherein said feedstock further comprises one or more additives selected from the group consisting of fats, medium chain triglycerides, flavors, sweeteners, colorings, humectants, fillers, emulsifiers, thickeners and mixtures thereof.

8. A consumable, gummy delivery system which comprises:

an elastic, continuous glycerylated gelatin matrix prepared by heating an aqueous solution of gelatin admixed with glycerin to a temperature and for a time sufficient to remove from about 10% to about 100% by weight of initial moisture content to provide a gummy glycerylated gelatin matrix as an elastic, water soluble solid; and one or more active ingredients in the form of a shearform matrix admixed with said glycerylated gelatin matrix, whereby said consumable gummy delivery system is formed which is readily soluble in aqueous media; wherein said shearform matrix is prepared by flash-flow processing.

9. A consumable, gummy delivery system which comprises:
   an elastic, continuous glycerylated gelatin matrix prepared by heating an aqueous solution of gelatin admixed with glycerin to a temperature and for a time sufficient to remove from about 10% to about 100% by weight of initial moisture content to provide a gummy glycerylated gelatin matrix as an elastic, water soluble solid; and
   one or more active ingredients in the form of a shearform matrix admixed with said glycerylated gelatin matrix, whereby said consumable gummy delivery system is formed which is readily soluble in aqueous media; wherein said gelatin is further provided as a component of a shearform matrix.

10. The delivery system of claim 9, wherein said shearform matrix for at least one of said active ingredient(s) and said gelatin further comprises a carrier material.

11. The delivery system of claim 10, wherein said carrier material is selected from the group comprising of saccharides, water soluble cellulosics and mixtures thereof.

12. A consumable gummy delivery system for an active which comprises:
   an elastic, continuous glycerylated gelatin matrix including an active-bearing shearform matrix carrier prepared by flash-flow processing, said shearform matrix carrier comprising a carrier material and an active ingredient.

13. A method of preparing a consumable gummy delivery system comprising:
   (i) providing an elastic, continuous glycerylated gelatin matrix;
   (ii) mixing said glycerylated gelatin matrix with an active ingredient to form a homogeneous mixture which is elastic, continuous and readily soluble in aqueous media;
   (iii) forming the resulting mixture into suitable chewable shapes.

14. The method of claim 13, wherein said glycerylated gelatin matrix is prepared by heating an aqueous solution of gelatin and glycerin to a temperature and for a time sufficient to remove from about 10% to about 100% of initial moisture of said gummy delivery system.

15. The method of claim 13, wherein said glycerylated gelatin matrix is present in an amount of from about 2% by weight to about 70% by weight of the gummy delivery system.

16. The method of claim 13, wherein said gelatin is present in an amount of from about 2% by weight to about 50% by weight of said gummy delivery system.

17. The method of claim 13, wherein said gelatin is present in an amount of from about 5% by weight to about 30% by weight of said gummy delivery system.

18. The method of claim 13, wherein said glycerine is present in an amount from about 4% by weight to about 60% by weight of said gummy delivery system.

19. The method of claim 13, wherein said glycerine is present in an amount from about 10% by weight to about 50% by weight of said gummy delivery system.

20. The method of claim 13, wherein said active ingredient is selected from the group consisting of medicaments, flavors, sweeteners and mixtures thereof.

21. The method of claim 20, wherein said medicament is selected from the group consisting of antitussives, antihistamines, decongestants, alkaloids, mineral supplements, laxatives, vitamins, antacids, ion exchange resins, anticholesterolemics, antilipid agents, antiarrhythmics, antipyretics, analgesics, appetite suppressants, expectorants, anti-inflammatory substances, coronary dilators, cerebral dilators, penpheral vasocilators, antiinfectives, psychotropics, antimanics, stimulants, gastrointestinal agents, sedatives, antidiarrheal preparations, antianginal drugs, vasodialators, antihypertensive drugs, vasoconstrictors and migraine treatments, antibiotics, tranquilizers, antipsychotics, antitumor drugs, anticoagulants and antithrombotic drugs, hypnotics antiemetics, antinauseants, anticonvulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, antiuricemic drugs, and mixtures thereof.

22. The method of claim 20, wherein said flavor is selected from the group consisting of natural flavors, artificial flavors and mixtures thereof.

23. The method of claim 22, wherein said natural flavors is selected from the group consisting of peppermint oil, spearmint oil, eucalyptus oil, cinnamon oil, menthol, oil of wintergreen (methylsalicylate), citrus oils, fruit essences and mixtures thereof.

24. The method of claim 22, wherein said artificial flavor is selected from the group of artificial sweeteners, synthetic flavor oils, aldehydes and esters.

25. The method claim 24, wherein said artificial sweetener is selected from the group consisted of saccharin, saccharin salts, cyclamic acid, cyclamic acid salts, aspartame, sucralose, acesulfame, and combinations thereof.

26. The method of claim 13, wherein comprising one or more additives admixed with said glycerylated gelatin matrix.

27. The method of claim 26, wherein said additive is selected from the group consisting of fats, medium chain triglycerides, sweeteners, flavors, colorings, humectants, fillers, emulsifiers, thickeners and mixtures thereof.

28. The method of claim 13, wherein said active ingredient is provided as a shearform matrix carrier prepared by flash flow processing a feedstock comprising an active ingredient and a carrier material.

29. The method of claim 28, wherein said carrier material is selected from the group consisting of saccharides, water soluble cellulosics and mixtures thereof.

30. The method of claim 29, wherein said saccharide is corn syrup solids.

31. The method of claim 27, wherein said feedstock further comprises one or more additives selected from the group consisting of fats, medium chain triglycerides, flavors, sweeteners, colorings, humectants, fillers, emulsifiers, thickeners and mixtures thereof.

32. The method of claim 13, further comprising a shearform matrix prepared by flash-flow processing.

33. The method of claim 13, wherein said gelatin is provided as a component of said shearform matrix.

34. The delivery system of claim 12, said delivery system having about 0% moisture.

35. The method of claim 14, wherein about 100% of initial moisture of said gummy delivery system is removed.

* * * * *